Figure 4:
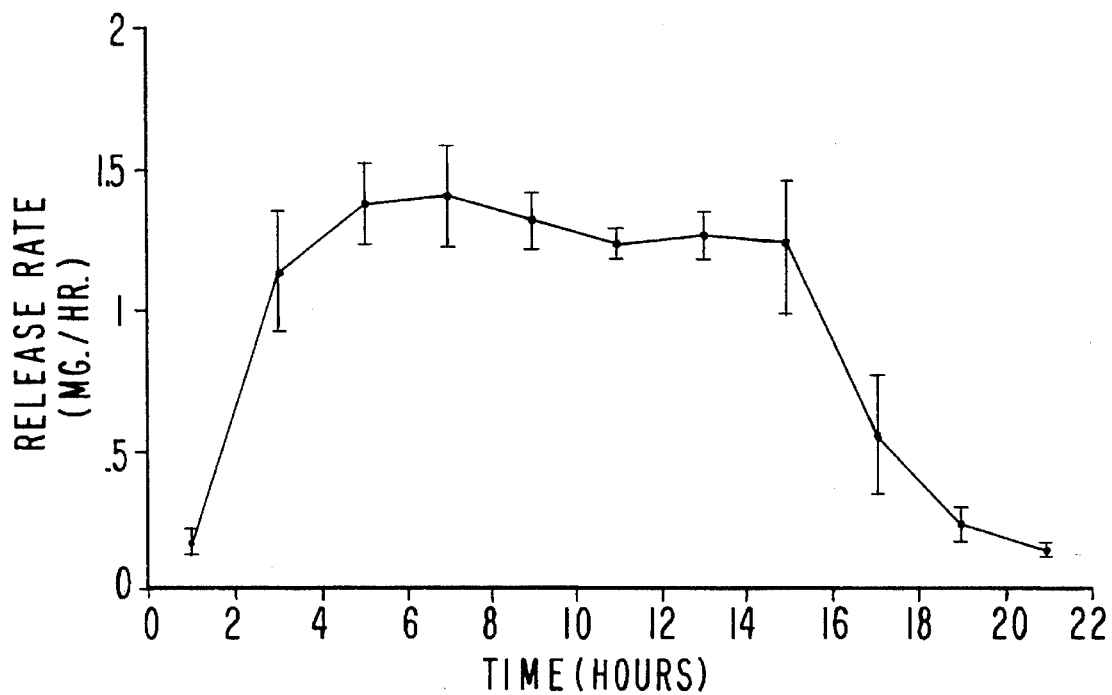

United States Patent

Kuczynski et al.

[11] Patent Number: 5,545,413
[45] Date of Patent: * Aug. 13, 1996

[54] DOSAGE FORM FOR ADMINISTERING ORAL HYPOGLYCEMIC GLIPIZIDE

[75] Inventors: Anthony L. Kuczynski; Atul D. Ayer; Patrick S. Wong, all of Palo Alto, Calif.

[73] Assignee: Alza Corporation, Palo Alto, Calif.

[*] Notice: The portion of the term of this patent subsequent to Jul. 2, 2008, has been disclaimed.

[21] Appl. No.: 650,822

[22] Filed: Jan. 22, 1991

Related U.S. Application Data

[62] Division of Ser. No. 402,314, Sep. 5, 1989, Pat. No. 5,024,843.

[51] Int. Cl.$^6$ .................... A61K 9/20; A61K 47/38; A61K 47/32; A61K 9/16
[52] U.S. Cl. .................... 424/473; 424/499; 424/501; 514/866
[58] Field of Search .................... 424/472, 473, 424/499, 501

[56] References Cited

U.S. PATENT DOCUMENTS

| | | | |
|---|---|---|---|
| 2,799,241 | 7/1957 | Wurster | 118/24 |
| 2,909,462 | 10/1959 | Warfield et al. | 167/56 |
| 3,845,770 | 11/1974 | Theeuwes et al. | 128/260 |
| 3,916,899 | 11/1975 | Theeuwes et al. | 128/260 |
| 4,016,880 | 2/1983 | Theeuwes et al. | 128/260 |
| 4,063,064 | 12/1977 | Saunders et al. | 219/121 L |
| 4,088,864 | 5/1978 | Theeuwes et al. | 219/121 LM |
| 4,200,098 | 4/1980 | Ayer et al. | 128/260 |
| 4,285,987 | 8/1981 | Ayer et al. | 427/3 |
| 4,627,851 | 12/1986 | Wong et al. | 424/473 |
| 4,673,405 | 6/1987 | Guittard et al. | 424/473 |
| 4,708,868 | 11/1987 | Brickl et al. | 424/80 |
| 4,803,076 | 2/1989 | Ranade | 424/438 |
| 4,851,232 | 7/1989 | Urquhart et al. | 424/469 |
| 4,902,514 | 2/1990 | Barclay et al. | 424/473 |
| 5,002,772 | 3/1991 | Curatolo et al. | 424/438 |
| 5,019,396 | 5/1991 | Ayer et al. | 424/473 |
| 5,024,843 | 6/1991 | Kuczynski et al. | 424/499 |
| 5,028,434 | 7/1991 | Barclay et al. | 424/473 |

OTHER PUBLICATIONS

Martindale, *The Extra Pharmacopoeia,* 29th Ed. (1989) p. 390.
*AHFS Drug Information,* (1989) pp. 1741–1745.
*J. Am. Phar. Assoc.,* Sci. Ed., vol. 48 (1959) pp. 451–459.
*J. Am. Phar. Assoc.,* Sci. Ed., vol. 49 (1960) pp. 82–84.
Remington's *Pharmaceutical Sciences,* 14th Ed., (1970) pp. 1626–1678.

*Primary Examiner*—Edward J. Webman
*Attorney, Agent, or Firm*—Paul L. Sabatine; Felissa H. Cagan; Mary Ann Dillahunty

[57] ABSTRACT

A dosage form is disclosed comprising the antidiabetic drug glipizide for administering to a patient in need of glipizide therapy.

7 Claims, 2 Drawing Sheets

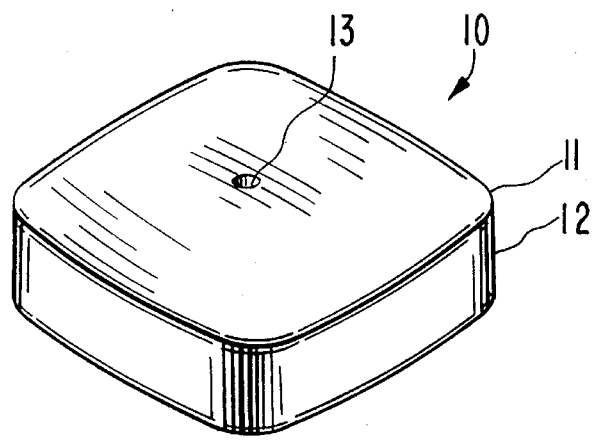
FIG_1
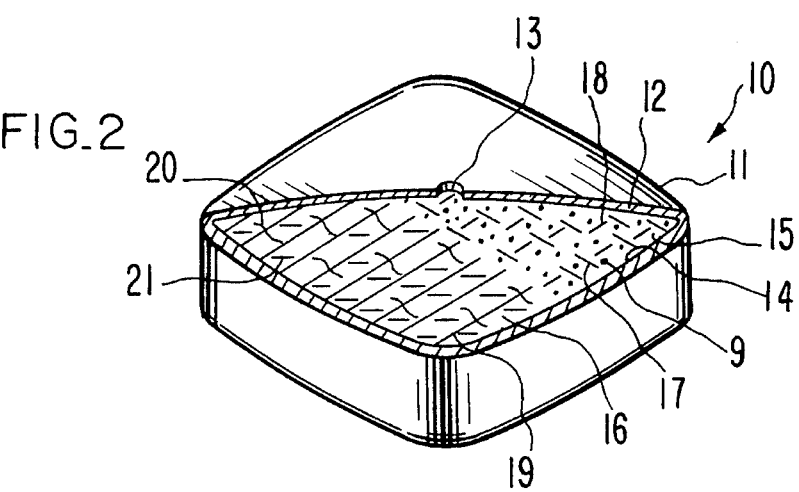
FIG_2
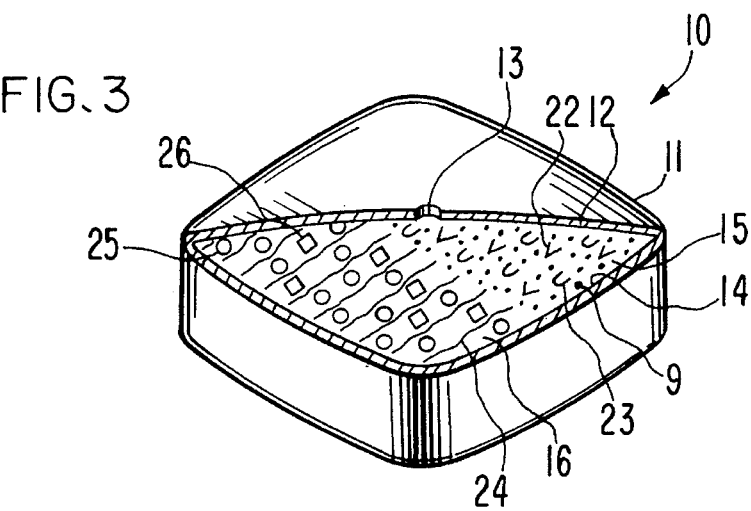
FIG_3

DOSAGE FORM FOR ADMINISTERING ORAL HYPOGLYCEMIC GLIPIZIDE

CROSS-REFERENCE TO RELATED APPLICATION

This application is a division of U.S. Ser. No. 07/402,314 filed Sep. 5, 1989, now U.S. Pat. No. 5,024,843, issued Jun. 18, 1991.

DISCLOSURE OF TECHNICAL FIELD

This invention pertains to a dosage form comprising the hypoglycemic drug glipizide. The invention concerns also a method for administering glipizide to a recipient in need of glipizide therapy.

DISCLOSURE OF BACKGROUND OF THE INVENTION

A clinical need exists for a dosage form for delivering an oral blood-glucose lowering drug to a patient needing this therapy. Glipizide is an oral blood-glucose lowering drug and it is indicated for the control of hyperglycemia and its associated symptomatology in patients with non-insulin dependent diabetes mellitus. Glipizide is useful therapeutically as an oral hypoglycemic drug because it stimulates insulin secretion from the beta cells of pancreatic-islet tissue, it increases the concentration of insulin in the pancreatic vein, and because it exhibits extrapancreatic action such as the ability to increase the number of insulin receptors.

Glipizide is known chemically as N-[2-[4-[[[(cyclohexylamino) carbonyl]amino]sulfonyl]phenyl]ethyl]-5-methylpyrazinecarboxamide. Glipizide is a white, odorless powder with a pKa of 5.9, and it is insoluble in both water and alcohol. These physical and chemical properties of glipizide do not lend the drug to formulation into a desage form that can administer glipizide at a controlled and known rate per unit time. The properties of glipizide are disclosed in *Martindale The Extra Pharmacopeia*, 29th Ed., p 390, (1989); and, *AHFS Drug Information*, pp 1741–45, (1989).

In the light of the above presentation, it will be appreciated by those versed in the pharmaceutical dispensing art to which this invention pertains, that a pressing need exists for a rate-controlled dosage form that can deliver the valuable drug glipizide to a patient in clinical need of blood-glucose lowering therapy. The pressing need exists also for an oral dosage form that can deliver glipizide at a controlled rate in a substantially constant dose per unit time for its beneficial therapeutic effects, and remain substantially independent of the changing environment of the gastrointestinal tract. It will be appreciated further by those skilled in the dispensing art, that if such a novel and unique dosage form is made available that can administer glipizide in a rate-controlled dose over time, and simultaneously provide blood-glucose lowering therapy, the dosage form would represent an advancement and a valuable contribution to the medical art.

DISCLOSURE OF OBJECTS OF THE INVENTION

Accordingly, in view of the above presentation, it is an immediate object of this invention to provide a dosage form for delivering glipizide in a rate controlled amount, and which dosage form substantially overcomes the deficiencies and omissions associated with the prior art.

Another object of the present invention is to provide a dosage form for orally administering glipizide in a rate-controlled dose for blood-glucose lowering therapy.

Another object of the invention is to provide a pharmaceutical dosage form that makes available controlled and sustained glipizide therapeutic activity to a patient in need of glipizide therapy.

Another object of the invention is to provide a novel dosage form manufactured as an osmotic device that can administer glipizide to a biological receptor site to produce the desired glipizide pharmacological effects.

Another object of the present invention is to provide a dosage form manufactured as an osmotic dosage form that maintains glipizide in the dosage form until released from the dosage form, thereby substantially reducing and/or substantially eliminating the unwanted influences of the gastrointestinal environment in use and still provide controlled administration of glipizide over time.

Another object of the present invention is to provide a dosage form that can deliver the aqueous insoluble drug glipizide at a controlled and beneficial known rate over time.

Another object of the present invention is to provide a dosage form adapted for the oral administration of glipizide and which dosage form comprise a first composition and a contacting second composition that operate in combination for the controlled administration of glipizide.

Another object of the present invention is to provide a complete pharmaceutical glipizide regimen comprising a composition comprising glipizide that can be dispensed from a drug delivery dosage form, the use of which requires intervention only for initiation and possibly for termination of the regimen.

Another object of the invention is to provide a method for treating hyperglycemia by orally administering glipizide in a rate-controlled dose per unit time to a warm-blooded animal in need of hyperglycemia therapy.

Other objects, features and advantages of this invention will be more apparent to those versed in the dispensing arts from the following detailed specification, taken in conjunction with the drawings and the accompanying claims.

BRIEF DISCLOSURE OF THE DRAWINGS

Figure 5:
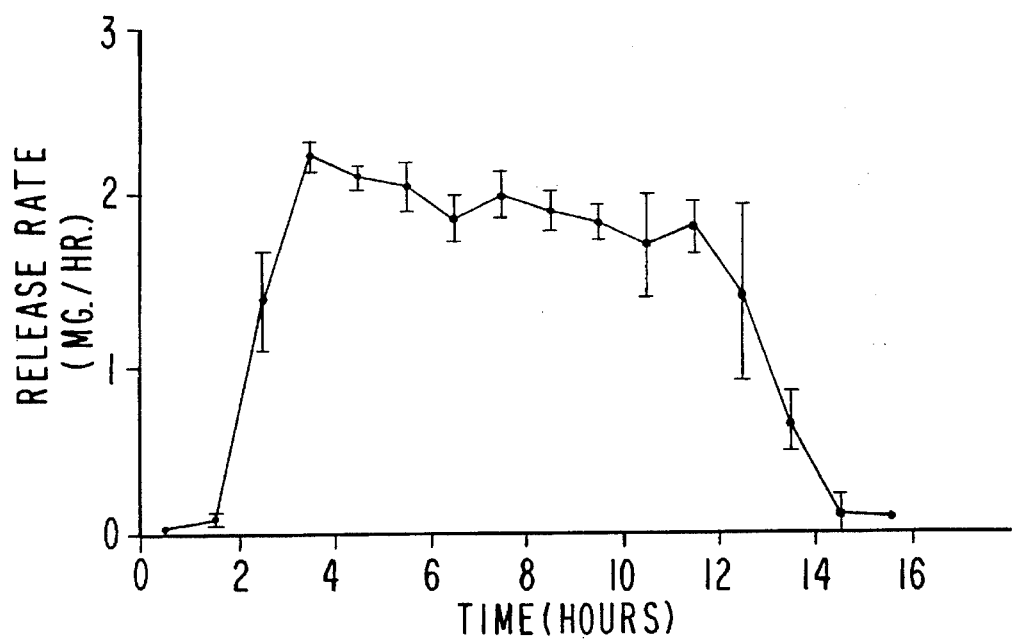

In the drawings, which are not drawn to scale, but are set forth to illustrate various embodiments of the invention, the drawing figures are as follows:

Drawing FIG. 1 is a view of a dosage form designed and shaped for orally administering glipizide to the gastrointestinal tract of a warm-blooded animal, including humans;

Drawing FIG. 2 is an opened view of the dosage form of drawing FIG. 1 illustrating the structure of the dosage form comprising glipizide;

Drawing FIG. 3 is an opened view of the dosage form of drawing FIG. 1 depicting a different internal structure embodiment provided by the invention;

Drawing FIG. 4 is a graph that depicts the release rate pattern from one embodiment of the dosage form provided by the invention; and, Drawing FIG. 5 is a graph that depicts the release rate pattern for a different embodiment of the dosage form provided by the invention.

In the drawing figures and in the specification like parts in related drawing figures are identified by like numbers. The terms appearing earlier in the specification and in the description of the drawings, as well as embodiments thereof, are further described elsewhere in the disclosure.

DETAILED DISCLOSURE OF THE DRAWING FIGURES

Turning now to the drawing figures in detail, which drawing figures are examples of the dosage forms provided by this invention, and which examples are not to be construed as limiting, one example of the dosage form is illustrated in drawing FIG. 1 and designated by the numeral 10. In drawing FIG. 1, dosage form 10 comprises a body 11, which body member 11 comprises a wall 12 that surrounds and encloses an internal compartment, not seen in drawing FIG. 1. Dosage form 10 comprises at least one exit means 13 for connecting the interior of dosage form 10 with the exterior environment of use.

In drawing FIG. 2, dosage form 10 is seen in opened view. In drawing FIG. 2, dosage form 10 comprises a body member 11 comprising wall 12, which wall surrounds and defines an internal compartment 14. Wall 12 comprises at least one exit means 13 that connects internal compartment 14 with the exterior of dosage form 10. Dosage form 10 can comprise more than one exit means 13. Wall 12 of dosage form 10 comprises in total, or in at least a part, a composition that is permeable to the passage of an exterior fluid present in the environment, and wall 12 is substantially impermeable to the passage of glipizide and other ingredients present in compartment 14. The composition comprising wall 12 is semipermeable, it is substantially inert, and wall 12 maintains its physical and chemical integrity during the dispensing life of glipizide from dosage form 10. The phrase, keeps its physical and chemical integrity," means wall 12 does not lose its structure, and it does not change chemically during the glipizide dispensing life of dosage form 10.

Wall 12, in a presently preferred embodiment, comprises 80 weight percent (wt %) to 100 weight percent of a composition comprising a cellulose polymer. The cellulose polymer comprises a member selected from the group consisting of a cellulose ester, cellulose ether, cellulose ester-ether, cellulose acylate, cellulose diacylate, cellulose triacylate, cellulose acetate, cellulose diacetate, and cellulose triacetate. Wall 12, in another preferred manufacture, comprises from 0 weight percent to 25 weight percent of a member selected from the group consisting of hydroxypropylcellulose and hydroxypropylmethylcellulose, and from 0 to 20 weight percent of polyethylene glycol, with the total amount of all wall-forming components comprising wall 12 equal to 100 weight percent.

Internal compartment 14 comprises an internal glipizide lamina 15, which glipizide lamina can be defined optionally as a glipizide composition 15. Internal compartment 14 also comprises an internal displacement lamina 16, which displacement lamina can be defined optionally as a displacement composition 16. The glipizide lamina 15 and the displacement lamina 16 initially are in laminar arrangement and they cooperate with each other and with dosage form 10 for the effective delivery of glipizide from dosage form 10.

The glipizide composition 15, in a presently preferred embodiment, as seen in FIG. 2, comprises about 2.0 mg to 50 mg of glipizide identified by dots 9; from 100 mg to 320 mg of a polyethylene oxide comprising 80,000 to 350,000 molecular weight and identified by dashes 17; from 5 mg to 50 mg of hydroxypropylmethylcellulose comprising a 9,200 to 22,000 molecular weight and identified by vertical lines 18; and from 0 mg to 7.5 mg of a lubricant such as stearic acid, magnesium stearate, and the like.

The displacement lamina 16, as seen in drawing FIG. 2, comprises 70 mg to 125 mg of a polyethylene oxide comprising a 4,000,000 to 8,000,000 molecular weight identified as lines 19; from 20 mg to 50 mg of an osmagent selected from the group consisting of sodium chloride and potassium chloride identified by wavy line 20; and from 5 mg to 15 mg of a hydroxypropylmethylcellulose having a 9,000 to 25,000 molecular weight identified by vertical slashes 21. Displacement lamina 16 optionally comprises from 0.1 mg to 5 mg of ferric oxide and from 0.01 mg to 5 mg of a lubricant such as magnesium stearate or stearic acid.

Drawing FIG. 3 depicts in opened section another osmotic dosage form 10 provided by the invention. In drawing FIG. 3, dosage form 10 comprises a body 11, a wall 12, which wall 12 surrounds an internal compartment 14 with an exit passageway 13 in wall 12. Internal compartment 14, in this dosage form, comprises an internal glipizide lamina 15, which glipizide lamina 15 comprises 2 mg to 25 mg of aqueous insoluble drug glipizide identified by dots 9; from 100 mg to 150 mg of a hydroxypropylcellulose comprising a 40,000 to 80,000 molecular weight identified by angle 22; and from 40 mg to 70 mg of a polyvinylpyrrol idone comprising a 30,000 to 70,000 molecular weight and identified by half circle 23. Internal compartment 14 comprises a displacement lamina 16 comprising 30 mg to 150 mg of sodium carboxymethylcellulose having 200,000 to 1,000,000 molecular weight identified by wavy lines 24; from 20 mg to 70 mg of an osmagent selected from the group consisting of sodium chloride and potassium chloride identified by circle 25; and from 0.5 mg to 10 mg of a hydroxypropylmethylcellulose comprising a 9,200 to 22,000 molecular weight identified by squares 26. Displacement lamina 16 optionally comprises from 0 mg to 5 mg of ferric oxide and optionally 0 mg to 7 mg of a lubricant.

The expression, "exit means 13," as used herein, comprises means and methods suitable for the controlled metered release of glipizide 9 from compartment 14 of dosage form 10. The exit means 13 comprises at least one passageway, orifice, or the like, through wall 12 for communication with glipizide 9 in compartment 14. The expression, "at least one passageway," includes aperture, orifice, bore, pore, or porous element through which glipizide can be released, or hollow fiber, capillary tube, porous overlay, porous insert, and the like. The expression also includes a material that erodes or is fluid-leached from wall 12 in a fluid environment of use to produce at least one pore-passageway of governed release rate pore-size in wall 12. Representative materials suitable for forming at least one passageway, or a multiplicity of passageways, comprise an erodible polyglycolic acid, or a polylactic acid member in wall 12, a gelatinous filament, polyvinyl alcohol, leachable materials such as a fluid removable pore forming polysaccharide, salt, oxide, polyol, or the like. A passageway or a plurality of passageways can be formed by leaching a material such as sorbitol, lactose, or the like, from wall 12. The passageway can have any shape such as round, triangular, square, elliptical, and the like, for assisting in the metered release of glipizide 9 from dosage form 10. Dosage form 10 can be constructed with one or more passageways in spaced apart relations, or more than one passageway on a single surface of dosage form 10. Passageways and equipment for forming passageways are disclosed in U.S. Pat. Nos. 3,845,770 issued November 1974 to Theeuwes et al; 3,916,899 issued November 1975 to Theeuwes et al; 4,016,880 issued April 1977 to Theeuwes et al; 4,063,064 issued December 1977 to Saunders et al; 4,088,864 issued May 1978 to Theeuwes et al; and, passageways formed by leaching are disclosed in U.S. Pat. Nos. 4,200,098 issued April 1980 to Ayer et al; 4,235,236 issued November 1980 to Theeuwes; and, 4,285,987 issued to Ayer et al.

Dosage form 10 of this invention is manufactured by standard techniques. For example, in one manufacture the drug glipizide is mixed with other composition-forming ingredients and the mix then pressed into a solid lamina possessing dimensions that correspond to the internal dimensions of the compartment space adjacent to the passageway. In another embodiment the beneficial drug glipizide and other composition forming ingredients and a solvent are mixed into a solid, or into a semisolid, by conventional methods such as ballmilling, calendering, stirring, or rollmilling, and then pressed into a preselected lamina forming shape. Next, a lamina composition comprising the osmopolymer and the osmagent are placed in contact with the lamina comprising the beneficial drug glipizide, and the two lamina comprising the laminate are surrounded with a semipermeable wall. The lamination of the glipizide composition and the osmopolymer displacement composition can be accomplished by using a two-layer tablet press technique. The wall can be applied by molding, spraying, or dipping the pressed shapes into wall-forming formulations. Another preferred technique that can be used for applying the wall is the air suspension coating procedure. This procedure consists in suspending and tumbling the two layered laminate in a current of air until the wall forming composition surrounds the laminate. The air suspension procedure is described in U.S. Pat. No. 2,799,241; in *J. Pharm. Assoc., Sci. Ed.*, Vol. 48 pp 451–59 (1959); and ibid, Vol. 49, pp 82–84, (1960). Other standard manufacturing procedures are described in *Modern Plastics Encyclopedia*, Vol. 46, pp 62–70, (1969); and in *Pharmaceutical Sciences*, by Remington, 14th Ed., pp 1626–1978, (1970), published by Mack Publishing Co., Easton, Pa.

Exemplary solvents suitable for manufacturing the wall, the laminate, and laminae, comprise inert inorganic and organic solvents that do not adversely affect the final wall and the final laminates. The solvents broadly comprise a member selected from the group consisting of aqueous solvents, alcohols, ketones, esters, ethers, aliphatic hydrocarbons, halogenated solvents, cycloaliphatics, aromatics, heterocyclic solvents, and mixtures thereof. Typical solvents comprise acetone, diacetone, alcohol, methanol, ethanol, isopropyl alcohol, butyl alcohol, methyl acetate, ethyl acetate, isopropyl acetate, n-butyl acetate, methyl isobutyl ketone, methylpropyl ketone, n-hexane, n-heptane, ethylene glycol monoethyl ether, ethylene glycol monoethyl acetate, methylene dichloride, ethylene dichloride, propylene dichloride, acetone and water, acetone and methanol, acetone and ethyl alcohol, methylene dichloride and methanol, ethylene dichloride and methanol, and the like.

DETAILED DISCLOSURE OF EXAMPLES OF THE INVENTION

The following examples are merely illustrative of the present invention, and they should not be considered as limiting the scope of this invention in any way, as these examples and other equivalents thereof will become apparent to those versed in the art in the light of the present disclosure, the drawings and the accompanying claims.

EXAMPLE 1

An oral dosage form, adapted, designed and shaped as an osmotic drug delivery system for admittance into the gastrointestinal tract of a patient in need of glipizide is manufactured as follows: first, 369 g of pharmaceutically acceptable hydroxypropylcellulose comprising a 60,000 average molecular weight is passed through a 20 mesh screen, followed by passing through a 40 mesh screen 162 g of pharmaceutically acceptable polyvinylpyrrolidone comprising a 40,000 average molecular weight. Next, the two screened ingredients are blended with 66 g of glipizide to form a homogeneous blend. The blend is suspended in a fluidized bed and sprayed with an atomized spray comprising an ethanol:water (70:30 vol:vol) solution until granules are formed of the three ingredients. The freshly prepared granules then are passed through a 20 mesh screen. Finally, the screened granulation is mixed with 3 g of magnesium stearate in a rollermill for 5 minutes.

Next, a separate hydrogel granulation is prepared as follows: first, 389 g of pharmaceutically acceptable sodium carboxymethylcellulose having 700,000 molecular weight, 174 g of sodium chloride, 30 g of pharmaceutically acceptable hydroxypropylmethylcellulose comprising a 11,200 molecular weight and 6 g of ferric oxide separately are screened through a 40 mesh screen. Then, all the screened ingredients are mixed to produce a homogeneous blend. Next, 300 ml of denatured anhydrous ethanol is added slowly to the blend with continuous mixing for about 5 minutes. The freshly prepared wet granulation is screened through a 20 mesh screen, allowed to dry at room temperature for 16 hours, and again passed through a 20 mesh screen. The screened granulation is mixed with 1.5 g of magnesium stearate in a rollermill for about 5 minutes.

Next, the glipizide granulation, and the hydrogel granulation are compressed into a bilaminate tablet arrangement. First, 200 mg of the glipizide composition is added to a 0.375 inch (9.5 mm) punch and tamped, then, 140 mg of the hydrogel granulation is added to the punch and the two laminae are pressed into a solid, contacting arrangement.

Next, the bilaminate is coated with a semipermeable wall. The semipermeable wall-forming composition comprises 93% cellulose acetate having a 39.8% acetyl content, and 7% polyethylene glycol having a 3350 molecular weight. The wall-forming composition is dissolved in a cosolvent comprising-acetone: water (90:10 wt:wt) to make a 4% solids solution. The wall-forming composition is sprayed onto and around the bilaminate in an Aeromatic® Air Suspension Coater.

Then, a 25 mil (0.635 mm) exit orifice is mechanically drilled on the glipizide side of the osmotic dosage form. The residual solvent is removed by drying the osmotic system for 48 hours at 50° C. and 50% humidity. The osmotic systems are dried for 1 hour at 50° C. to remove excess moisture. Attached drawing FIG. 4 shows the in vitro release rate profile for glipizide from the finished osmotic system as released in distilled water. The error bars represent the standard deviation added to and subtracted from the mean of five osmotic delivery system. An osmotic dosage form provided by the invention comprises 11 wt % glipizide, 61.50 wt % hydroxypropylcellulose of 60,000 molecular weight, 27.0 wt % polyvinylpyrrolidone of 40,000 molecular weight, 0.5% magnesium stearate in the glipizide composition; 64.8 wt % sodium carboxymethylcellulose of 700,000 molecular weight, 29 wt % sodium chloride, 5 wt % hydroxypropylmethylcellulose of 11,200 molecular weight and 1.0 wt % ferric oxide, 0.2% magnesium stearate in the hydrogel composition; and, 93.0 cellulose acetate having a 39.8% acetyl content, and 7.0 polyethylene glycol having a 3350 molecular weight in the semipermeable wall formulation.

EXAMPLE 2

A dosage form adapted, designed and shaped as an osmotic drug delivery system is manufactured as follows: first, a glipizide composition is provided by blending together into a homogeneous blend 478 g of pharmaceutically acceptable polyethylene oxide comprising a 200,000 molecular weight, 66 g of glipizide and 54 g of pharmaceutically acceptable hydroxypropylmethylcellulose comprising a 11,200 molecular weight. Then, 425 ml of denatured anhydrous ethanol is added slowly with continuous mixing over 5 minutes. The freshly prepared wet granulation is screened through a 20 mesh screen, dried at room temperature for 16 hours, and again screened through a 20 mesh screen. Finally, the screened granulation is mixed with 1.5 g of magnesium stearate in a rollermill for 5 minutes.

Next, a hydrogel composition is prepared as follows: first, 412.5 g of pharmaceutically acceptable polyethylene oxide comprising a 7,500,000 molecular weight, 150 g of sodium chloride and 6 g of ferric oxide separately are screened through a 40 mesh screen. Then, all the screened ingredients are mixed with 30 g of hydroxypropylmethylcellulose comprising a 11,200 molecular weight to produce a homogeneous blend. Next, 300 mg of denatured anhydrous alcohol is added slowly to the blend with continuous mixing for 5 minutes. The freshly prepared wet granulation is passed through a 20 mesh screen, allowed to dry at room temperature for 16 hours, and again passed through a 20 mesh screen. The screened granulation is mixed with 1.5 g of magnesium stearate in a rollermill for 5 minutes.

Next, the glipizide composition and the hydrogel composition are compressed into bilaminate tablets. First, 200 mg of the glipizide is added to a 0.375 inch (9.5 mm) punch and tamped, then, 140 mg of the hydrogel composition is added and the laminae are pressed under a pressure head of 2 tons into a contacting laminated arrangement.

Then, the bilaminate arrangements are coated with a semipermeable wall. The wall forming composition comprises 93% cellulose acetate having a 39.8% acetyl content, and 7% polyethylene glycol having a molecular weight of 3350. The wall-forming composition is dissolved in an acetone:water (90:10 wt:wt) cosolvent to make a 4% solids solution. The wall forming composition is sprayed onto and around the bilaminate in an Aeromatic® Air Suspension Coater.

Next, a 25 mil (0.635 mm) exit passageway is mechanically drilled through the semipermeable wall to connect the glipizide drug lamina with the exterior of the dosage system. The residual solvent is removed by drying for 48 hours at 50° C. and 50% humidity. Next, the osmotic systems are dried for 1 hour at 50° C. to remove excess moisture. The dosage form produced by this manufacture provides a glipizide composition comprising 11 wt % glipizide, 79.7 wt % polyethylene oxide of 200,000 molecular weight, 9 wt % hydroxypropylmethylcellulose of 11,200 molecular weight, and 0.3 wt % magnesium stearate; a hydrogel composition comprising 68.8 wt % polyethylene oxide comprising a 7,500,000 molecular weight, 25 wt % sodium chloride, 5 wt % hydroxypropylmethylcellulose, 1.0 wt % ferric oxide and 0.2 wt % magnesium stearate; and a semipermeable wall comprising 93 wt % cellulose acetate comprising a 39.8% acetyl content, and 7.0 wt % polyethylene glycol comprising a 3350 molecular weight.

Accompanying drawing FIG. 5 depicts the in vitro release rate profile of glipizide released from the final dosage form for four dosage forms. The error bars represent the standard deviation added to and subtracted from the mean of the dosage form.

DISCLOSURE OF A METHOD OF USING THE INVENTION

An embodiment of the invention pertains to a method for delivering the beneficial drug glipizide orally at a controlled rate to a warm blooded animal in need of glipizide therapy, which method comprises the steps of: (A) admitting into the warm-blooded animal a dosage form comprising: (1) a wall surrounding a compartment, the wall comprising at least in part a semipermeable polymeric composition permeable to the passage of fluid and substantially impermeable to the passage of glipizide; (2) a pharmaceutically acceptable composition in the compartment comprising about 2.5 mg to 50 mg of hypoglycemic glipizide for performing an antidiabetic program; (3) a hydrogel composition in the compartment comprising a member selected from the group consisting of a polyethylene oxide having a 4,000,000 to 7,500,000 molecular weight and a sodium carboxymethylcellulose having a 200,000 to 1,000,000 molecular weight for imbibing and absorbing fluid for pushing the glipizide composition from the dosage form; and, (4) at least one passageway in the wall for releasing glipizide; (B) imbibing fluid through the semipermeable wall at a rate determined by the permeability of the semipermeable wall and the osmotic pressure gradient across the semipermeable wall causing the hydrogel composition to expand and swell; and (C) delivering the beneficial glipizide from the dosage form through the exit passage to the warm blooded animal over a prolonged period of time to produce the desired hypoglycemic effect.

In summary, it will be appreciated that the present invention contributes to the art an unexpected and unforseen dosage form that possesses the practical utility for administering aqueous insoluble glipizide from an osmotic dosage form at a dose metered release rate per unit time. While the invention has been described and pointed out in detail with reference to operative embodiments thereof it will be understood that those skilled in the art that various changes, modifications, substitutions and omissions can be made without departing from the spirit of the invention. It is intended, therefore, that the invention embrace those equivalents within the scope of the claims which follow.

We claim:

1. A method for controlling hyperglycemia and its associated symptomatology in a patient in need of glipizide therapy for controlling same, wherein the method comprises:

(a) admitting orally into the patient a dosage form comprising:

(1) a wall comprising at least at part a composition permeable to the passage of fluid, which wall surrounds;

(2) a compartment;

(3) a lamina in the compartment comprising about 2.0 mg to 50 mg of glipizide and a polyethylene oxide comprising an 80,000 to 350,000 molecular weight;

(4) a displacement lamina in the compartment comprising a polyethylene oxide comprising a 4,000,000 to 8,000,000 molecular weight, which displacement lamina imbides fluid, expands and displaces the lamina comprising the glipizide from the compartment;

(5) at least one exit means in the wall for delivering glipizide from the dosage form;

(b) imbibing fluid into the dosage form for contacting the displacement lamina comprising the polyethylene oxide causing it to expand and displace the lamina comprising the glipizide; thereby, (c) delivering a therapeutically effective amount of glipizide to the patient to produce the intended effects.

2. A method for controlling hyperglycemia and its associated symptomatology in a patient in need of glipizide therapy for controlling same, wherein the method comprises:

(a) admitting orally into the patient a dosage form comprising:
  (1) a wall comprising at least in part a composition permeable to the passage of fluid, which wall surrounds;
  (2) a compartment;
  (3) a lamina in the compartment comprising about 2.0 mg to 50 mg of glipizide and a polyethylene oxide comprising an 80,000 to 350,000 molecular weight;
  (4) a displacement lamina in the compartment comprising sodium carboxymethylcellulose comprising a 200,000 to 1,000,000 molecular weight, which displacement lamina imbibes fluid, swells and pushes glipizide from the compartment;
  (5) at least one exit means in the wall for delivering glipizide from the dosage form;

(b) imbibing fluid by the sodium carboxymethylcellulose causing it to expand and push the glipizide from the dosage form; thereby, (c) delivering a therapeutically effective amount of glipizide to the patient to produce the intended effects.

3. A dosage form for administering glipizide to a patient, wherein the dosage form comprises:

(a) a wall permeable at least in part to the passage of an exterior fluid, which wall surrounds:
(b) a compartment;
(c) a lamina in the compartment comprising from 2 mg to 50 mg of glipizide and a polyethylene oxide comprising a 80,000 to 350,000 molecular weight;
(d) a displacement lamina in the compartment comprising a polyethylene oxide comprising a 4,000,000 to 8,000,000 molecular weight; and,
(e) at least one exit passageway in the wall for connecting the exterior with the interior of the dosage form for delivering glipizide to the patient.

4. The dosage form for administering glipizide to the patient according to claim 3, wherein the patient is a diabetic and the wall of the dosage form is permeable in at least a part to the passage of fluid and comprises a member selected from the group consisting of a cellulose acylate, cellulose diacylate, cellulose triacylate, cellulose acetate, cellulose diacetate, and cellulose triacetate, and wherein the wall comprises at least one exit for delivering the glipizide from the dosage form.

5. A dosage form for delivering an antidiabetic glipizide for lowering blood glucose in a patient in need of lowering blood glucose therapy, wherein the dosage form comprises:

(a) a pharmaceutically acceptable wall comprising a composition permeable in at least a part to the passage of fluid, which wall surrounds:
(b) a compartment;
(c) a first lamina in the compartment comprising from 2 mg to 50 mg of glipizide, a polyethylene oxide and a hydroxypropylmethylcellulose comprising a 9,000 to 25,000 average molecular weight;
(d) a second displacement lamina in the compartment comprising a polyethylene oxide polymer comprising a 4,000,000 to 8,000,000 molecular weight; and
(e) at least one passageway in the wall for connecting the exterior with the interior of the dosage form for delivering glipizide from the dosage form to the patient.

6. The dosage form for delivering the antidiabetic glipizide to the patient according to claim 5, wherein the passageway is formed by leaching to provide a passageway of controlled porosity.

7. A dosage form for delivering an antidiabetic drug glipizide to a patient in need of hypoglycemic action, wherein the dosage form comprises:

(a) a pharmaceutically acceptable wall permeable to the passage of a fluid present in the patient, which wall surrounds;
(b) a compartment;
(c) a first lamina in the compartment comprising from 2 mg to 50 mg of glipizide, a hydroxypropylcellulose polymer and a polyvinylpyrrolidone polymer;
(d) a second displacement lamina in the compartment, the displacement lamina comprising sodium carboxymethylcellulose, and hydroxypropylmethylcellulose; and
(e) at least one passageway in the wall for connecting the exterior with the interior of the dosage form for delivering the glipizide from the dosage form to the patient.

\* \* \* \* \*

UNITED STATES PATENT AND TRADEMARK OFFICE
CERTIFICATE OF CORRECTION

PATENT NO. : 5,545,413
DATED : August 13, 1996
INVENTOR(S) : Anthony L. Kuczynski, Atul D. Ayer, Patrick S. Wong It is certified that error appears in the above-indentified patent and that said Letters Patent is hereby corrected as shown below:

Col. 8,
Claim 1, line 59, "imbides" should read --imbibes--; Col. 9, claim 2, line 19, "sweils" should read --swells--.

Signed and Sealed this

Fifth Day of November, 1996

BRUCE LEHMAN

Attest:

Attesting Officer

Commissioner of Patents and Trademarks